United States Patent [19]
Maclay et al.

[11] Patent Number: 5,716,506
[45] Date of Patent: Feb. 10, 1998

[54] ELECTROCHEMICAL SENSORS FOR GAS DETECTION

[75] Inventors: G. Jordan Maclay, Maywood; Darioush Keyvani, Northbrook, both of Ill.; Sung B. Lee, Dongjak-ku, Rep. of Korea

[73] Assignee: Board of Trustees of the University of Illinois, Urbana, Ill.

[21] Appl. No.: 540,005

[22] Filed: Oct. 6, 1995

[51] Int. Cl.$^6$ ................................................. G01N 27/407
[52] U.S. Cl. .......................... 204/424; 204/425; 204/426; 205/784
[58] Field of Search ........................ 204/421–429

[56] References Cited

U.S. PATENT DOCUMENTS

| | | | |
|---|---|---|---|
| 3,539,455 | 11/1970 | Clark | 205/778 |
| 4,288,544 | 9/1981 | Suzuki et al. | 204/415 |
| 4,388,155 | 6/1983 | Chamberland et al. | 204/427 |
| 4,394,222 | 7/1983 | Rohr | 204/427 |
| 4,900,405 | 2/1990 | Otagawa et al. | 204/412 |

OTHER PUBLICATIONS

A. M. Azad et al., *J. Electrochem. Soc.*, vol. 139, No. 12, pp. 3690–3704 (1992) month unavailable.

W. Buttner et al., *Sensors and Materials*, vol. 2., No. 2, pp. 99–106 (1990) month unavailable.

S. B. Lee et al., *J. Electrochem. Soc.*, vol. 142., No. 1, pp. 157–160, (1995) month unavailable.

K. Lundstrom et al., *J. Appl. Phys.*, vol. 46., No. 9, pp. 3876–3881 (1975) month unavailable.

T. Otagawa et al., *Sensors and Actuators*, vol. B1, pp. 319–325 (1990) month unavailable.

V. Schoenberg et al., *Sensors and Actuators*, vol. B1, No. 1–6, pp. 58–61 (1990) month unavailable.

K. A. Seiyama et al., *J. Anal. Chem.*, vol. 34, No. 11, pp. 1502–1503 (1962) month unavailable.

A. Yasuda et al., *J. Electrochem. Soc.*, vol. 139, No. 4, pp. 1091–1095 (1992) month available.

Hockh's Chemical Dictionary, 4th ed., 1969 month unavailable, p. 529.

*Primary Examiner*—T. Tung
*Attorney, Agent, or Firm*—Marshall, O'Toole, Gerstein, Murray & Borun

[57] ABSTRACT

Amperometric electrochemical sensors for detection of an analyte gas in air are disclosed. The sensors can be used in a gas detector to detect the analyte gas and to compensate for the relative humidity and temperature of the air. In addition, an electrochemical sensor having high surface area electrodes, and an increased sensitivity, is disclosed.

6 Claims, 5 Drawing Sheets

ELECTROCHEMICAL SENSORS FOR GAS DETECTION

FIELD OF THE INVENTION

The present invention relates to electrochemical sensors for the detection of a predetermined gas, such as carbon monoxide, in air. In particular, the present invention relates to microfabricated sensors that compensate for relative humidity and temperature of the air in the detection of a predetermined gas in air. The present invention also relates to electrochemical sensors having high surface area electrodes which enhance the sensitivity of the sensors to the predetermined gas.

BACKGROUND OF THE INVENTION

Hydrogen-sensitive, palladium-gate field effect transistor (FET) structures have been known for several years, and were among the first gas-sensitive devices fabricated using "microfabrication technology." Microfabrication technology is the technology used to manufacture integrated circuits. Various investigators have disclosed different gas-sensitive microstructures, but very few of these devices have been successfully commercialized. Furthermore, almost all of the gas-sensitive devices commercially available today are manufactured using "conventional technology," as opposed to using "microfabrication technology." Conventional technology is used because of unsolved problems encountered in past investigations of microfabricated gas sensors.

In particular, K. Lundstrom et al., *J. Appl. Phys.*, 46 (1975), pages 3876–3881, was the first publication directed to a gate-sensitive FET structure. The Lundstrom et al. publication described the effects of hydrogen ions in water on the drain current of an FET whose gate had been removed. It was theorized, therefore, that the batch production methods of microfabrication could be used to mass produce low cost, tightly controlled, gas sensors. However, the problem of electrode blistering at high hydrogen concentration, and the problem of long-term stability of the electrode interface at elevated temperatures, were encountered. Multimetal electrodes then were proposed to help overcome the blistering and stability problems.

Another approach to achieve desired electrode stability was the development of a special switched capacitor circuit that measured the total charge under the MOS Capacitance-Voltage curve, i.e., from accumulation to inversion, at a rate of about 60KHz (V. Schoenberg et al., *Sensors and Actuators*, Vol. B1, No. 1–6, (1990), pages 58–62). The change in the integral of this charge provides an indication of hydrogen concentration. Presently, FET-based hydrogen sensors are commercially available in small quantities from various sources. It also has been reported that this type of sensor is manufactured in China for use in the electrical power industry.

A more common sensor is the Figaro sensor. The response of a Figaro sensor is based on the change in conductivity of doped tin oxide upon exposure to hydrogen, methane, and various organic vapors. It was theorized that batch microfabrication methods could improve this sensor by reducing cost while improving quality control and performance. Numerous researchers attempted to microfabricate the tin oxide sensors, but to date, the Figaro sensors remain the sensors of choice in the market place. See, for example, K. Seiyama et al., *J. Anal. Chem.*, Vol. 34, (1962), pages 1502–1506 and A. M. Azad et al., *J. Electrochem. Soc.*, Vol. 139 (1992), pages 3690–3694.

In various attempts at microfabrication of sensors, investigators have encountered extensive problems in obtaining the correct morphology and stoichiometry of the tin oxide, in stabilizing the sensor for long-term operation at elevated temperatures, in obtaining reproducible performance, and in thermally isolating the sensor for low power operation. Using conventional technology, a very small tin oxide bead or cylinder is formed and suspended in space, thereby eliminating many of the problems encountered in the microfabricated approach.

Presently, there are numerous manufacturers of amperometric electrochemical sensors. The sensors are used to detect a broad variety of gasses such as carbon monoxide (CO), hydrogen sulfide ($H_2S$), nitrogen oxides ($NO_x$), like nitric oxide (NO) and nitrogen dioxide ($NO_2$), and chlorine ($Cl_2$), for example. These electrochemical sensors rely upon an aqueous electrolyte, such as sulfuric acid, in a plastic cell containing a working electrode (WE) and counter electrode (CE), and optionally a reference electrode (RE). The electrodes do not encounter a significant relative humidity effect because the aqueous electrolyte saturates the air surrounding the electrodes. Because the conventionally fabricated electrochemical sensors are commercially successful, it would be advantageous to utilize the chemistry of these sensors in a microfabricated structure.

The present invention, therefore, is directed to providing a microfabricated electrochemical sensor to detect a predetermined gas in air. The electrochemical sensors have the ability to compensate for the relative humidity and temperature of the air. In addition, it would be an advance in the art to provide a microfabricated sensor having a substantially increased sensitivity to a predetermined gas in air.

SUMMARY OF THE INVENTION

The present invention relates to microfabricated electrochemical sensors used in gas detection. In particular, the present invention is directed to planar, microfabricated sensors having an ability to compensate for the effects of the relative humidity and temperature of the air in the detection of a predetermined gas. The present invention also is directed to increasing the sensitivity of electrochemical sensors used in gas detection by employing high surface area electrodes.

The present electrochemical sensors are planar, microfabricated sensors having photolithographically defined thin film electrodes, such as platinum electrodes, coated with a polymer electrolyte film. The polymer electrolyte is capable of conducting electricity at room temperature, i.e., about 25° C.

In accordance with an important aspect of the present invention, the conductivity of the polymer electrolyte varies with the relative humidity. Therefore, the relative humidity effects on the electrochemical sensors are compensated by using a reference sensor. The reference sensor compensates for the effects of relative humidity by utilizing electrodes that are inert with respect to the predetermined gas being detected and that are coated with the polymer electrolyte.

As an example, for a module designed to detect carbon monoxide, the active sensor has platinum electrodes capable of detecting carbon monoxide, and coated with a polymer electrolyte. The reference sensor has electrodes that are inert to carbon monoxide, e.g., manufactured from gold, and are coated with the same polymer electrolyte. Therefore, the active sensor detects the carbon monoxide and also exhibits a background response related to relative humidity and temperature of the air. The reference sensor is sensitive only to the relative humidity and temperature of the air. The response of the reference sensor then is subtracted from the response of the active sensor, and an accurate determination of carbon monoxide concentration in air results.

In accordance with another important aspect of the present invention, a microfabricated sensor having high surface area electrodes is utilized to increase sensor sensitivity in the detection of a predetermined gas. For example, in the detection of carbon monoxide, using high surface area platinum electrodes provides a signal that is forty times greater than the signal obtained with low surface area platinum electrodes.

Therefore, an important aspect of the present invention is to provide a gas detector to assay for the presence and concentration of an analyte gas in air, said detector comprising:

(a) a substrate;
(b) an active sensor secured to the substrate, said active sensor comprising:
  (i) a first working electrode comprising a first electrode material, wherein the first electrode material is capable of detecting the analyte gas,
  (ii) a first counter electrode comprising the first electrode material, and
  (iii) a layer of a polymer electrolyte applied over the first working electrode and the first counter electrode, said active sensor capable of generating a detectable response to the analyte gas, relative humidity, and temperature;
(c) a reference sensor secured to the substrate, said reference sensor comprising:
  (i) a second working electrode comprising a second electrode material, wherein the second electrode material is inert with respect to the analyte gas,
  (ii) a second counter electrode comprising the second electrode material, and
  (iii) a layer of the polymer electrolyte applied over the second working electrode and the second counter electrode, said reference sensor capable of generating a detectable response to relative humidity and temperature; and
(d) means operatively connected to the active sensor and the reference sensor to correlate the response of the active sensor and the response of the reference sensor to provide an assay for the analyte gas that compensates for the relative humidity and temperature.

Another important aspect of the present invention is to provide a method of determining the presence or concentration of an analyte gas in air comprising:

(a) contacting an air sample with an active sensor to generate a detectable response, said active sensor comprising
  (i) a second working electrode comprising a second electrode material, wherein the second electrode material is inert with respect to the analyte gas,
  (ii) a second counter electrode comprising the second electrode material,
  (iii) a layer of the polymer electrolyte applied over the second working electrode and the second counter electrode, said reference sensor capable of generating a detectable response to relative humidity and temperature, and
  (iv) means operatively conducted to the first working electrode and the first counter electrode for measuring a change in conductivity, and providing a detectable response said active sensor capable of generating a detectable response to the analyte gas, relative humidity, and temperature;

(b) simultaneously contacting the air sample with a reference sensor to generate a detectable response, said reference sensor comprising
  (i) a second working electrode comprising a second electrode material, wherein the second electrode material is inert with respect to the analyte gas,
  (ii) a second counter electrode comprising the second electrode material,
  (iii) a layer of the polymer electrolyte applied over the second working electrode and the second counter electrode, said reference sensor capable of generating a detectable response to relative humidity and temperature, and
  (iv) means operatively connected to the second working electrode and the second counter electrode for measuring a change in conductivity, and providing a detectable response said reference sensor capable of generating a detectable response to relative humidity and temperature; and (c) correlating the response of the active sensor to the response of the reference electrode to compensate for the relative humidity and temperature of the air and provide a compensated response; and (d) correlating the compensated response to the concentration of the analyte gas in the air sample.

Yet another important aspect of the present invention is to provide an electrochemical sensor to detect the presence and concentration of a predetermined gas in air, said sensor comprising:

(a) a substrate;
(b) two high surface area electrodes deposited on a surface of the substrate; and
(c) a film of a polymer electrolyte applied the electrodes.

BRIEF DESCRIPTION OF THE DRAWINGS

The above and other aspects and advantages of the present invention will become apparent from the following detailed description of the preferred embodiments, as illustrated in the accompanying figures, wherein.

DETAILED DESCRIPTION OF THE PREFERRED EMBODIMENTS

Figure 1:
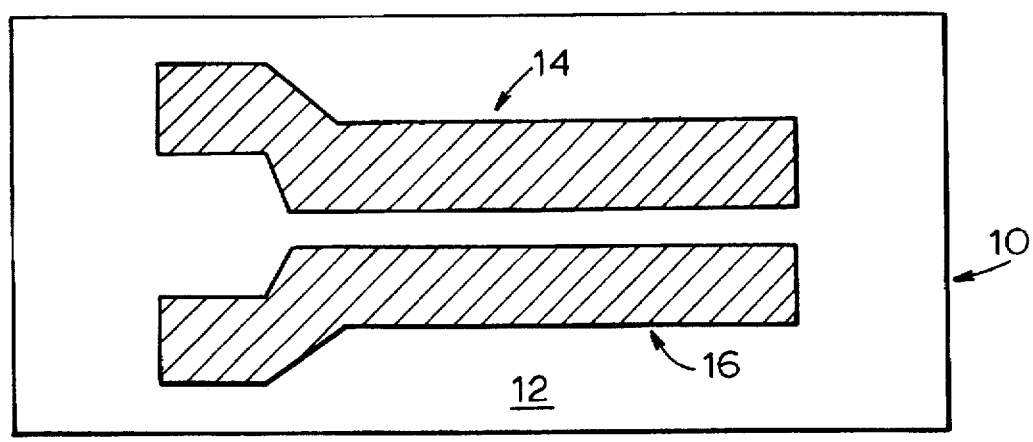
FIG. 1 is a top view of one embodiment of an electrochemical sensor of the present invention.

The following discussion is directed primarily to sensors used in the detection of carbon monoxide in air. However, the detection of carbon monoxide discussed herein is used for illustrative purposes only. As discussed hereafter, persons skilled in the art of designing electrochemical sensors are capable of adapting the teachings of the present invention to detect any one of a variety of predetermined gases in air. Accordingly, the present invention is not limited to carbon monoxide sensors.

In general, gas detectors of the present invention comprise: (a) an active sensor, and (b) a reference sensor. The active sensor is capable of responding to the predetermined gas. The active sensor also responds to relative humidity and temperature, thereby providing a background signal. The reference sensor is inert with respect to the predetermined gas, but does respond to the relative humidity and temperature of the air. The reference sensor signal, therefore, is used to compensate for relative humidity and temperature by eliminating the background signal in the active sensor.

The thin film electrodes of the active sensor are manufactured from an electrode material that is responsive to the predetermined gas, for example platinum in the detection of carbon monoxide. The reference sensor also has thin film electrodes, but the electrodes are manufactured from an electrode material that is inert with respect to the predetermined gas, for example gold in the detection of carbon monoxide. The electrodes are deposited and shaped on a substrate using standard photolithography. One electrode of each sensor is termed the counter electrode (CE) and the other electrode is termed the working electrode (WE). In accordance with an important feature of the present invention, a reference electrode is optional, and can be omitted without adversely affecting the detection of a particular predetermined gas.

With respect to detecting carbon monoxide (CO) in air, a potential is applied over the electrodes (i.e., a bias) which makes the WE positive with respect to the CE, for example, by about 0.1 to about 0.3 volts. The optimum potential varies with the particular predetermined gas to be detected. Persons skilled in the art are aware of, or can determine, the optimum potential for different gases, which for carbon monoxide is about −0.3 to about +0.3 volts.

In the detection of carbon monoxide, the following half reactions occur at the electrodes of the active sensor:

(1) oxidation of the carbon monoxide at the WE $$CO + H_2O \rightarrow CO_2 + 2H^+ + 2e^-$$

(2) reduction of oxygen at the CE $$2H^+ + 2e^- + \tfrac{1}{2}O_2 \rightarrow H_2O$$

The net effect of the two half reactions is:

$$CO + \tfrac{1}{2}O_2 \rightarrow CO_2$$

Similar half reactions do not occur at the electrodes of reference sensor because gold is inert with respect to detecting carbon monoxide.

For the half reactions to balance, a proton (i.e., $H^+$ ion) must be transported from the WE to the CE. This can occur because in the manufacture of the sensor, a working electrode (WE) and a counter electrode (CE) are patterned on the substrate surface, then an electrically conducting polymer electrolyte is deposited as a film over the electrodes. The polymer electrolyte is in a hydrogen form which is capable of conducting protons.

More particularly with respect to carbon monoxide detection, a bias of about −0.3 to about +0.3 volts is applied across the WE and CE of the active sensor and the reference sensor. The electrodes have been coated with a polymer electrolyte film. A small current flows, and in the presence of carbon monoxide, the current increases as the carbon monoxide concentration increases. Typical currents are about 10 to about 50 nanoamps per ppm of carbon monoxide. The current across the electrodes of the reference sensor does not increase with carbon monoxide concentration. An increase in sensitivity of the active sensor to carbon monoxide was observed when a high surface area electroactive material was electrodeposited on top of the microfabricated electrodes. As illustrated below, the sensitivity is enhanced by a factor of forty in comparison to microfabricated carbon monoxide sensors having low surface area electrodes.

As previously stated, numerous problems have been encountered in the microfabrication of electrochemical sensors used to detect a predetermined gas in air. These problems include finding an electrolyte compatible with microfabrication methods, adhesion and corrosion of the electrodes in the electrolyte environment, obtaining a sufficient signal, long-term stability of the electrode-electrolyte interface, and compensating for the effects of relative humidity and temperature of the air. As illustrated hereafter, the present electrochemical sensors overcome these unsolved problems.

In particular, the present electrochemical sensors are prepared by photolithographically applying a suitable electrode material to a substrate. The substrate can be smooth, e.g., alumina or a polymer, like a polytetrafluoroethylene, or rough, e.g., silicon dioxide. Sensor substrates are well known to persons skilled in the art and are selected based upon the material of construction of the electrode and the particular predetermined gas to be detected.

A suitable electrode material is photolithographically applied to the substrate by methods well known in the art. The choice of electrode material is directly related to the identity of the gas being detected. The electrode material of the active sensor is responsive to the predetermined gas. The electrode material of the reference sensor is inert to the predetermined gas. Typically, the electrode material is a noble metal, like platinum or gold, however, other materials, such as carbon, can serve as the electrode material. In the detection of carbon monoxide, the electrode material of the active sensor preferably is platinum, and the electrode material of the reference sensor preferably is gold.

Next, a polymer electrolyte is applied, as a coating or film, over the electrodes. One example of a suitable polymer electrolyte is NAFION® 117, available from E.I. DuPont de Nemours, Wilmington, Del. NAFION® 117 is a suitable polymer electrolyte because it is relatively inert chemically, and is a stable electrolyte having physical properties amenable to microfabrication techniques. A suitable polymer electrolyte has the ability to conduct electricity at 25° C. and is in a chemical form such that protons can be transported. Accordingly, the polymer electrolyte preferably is in the acidic form and contains acidic moieties capable of transporting protons.

In particular, the hydrogen form of a polymer electrolyte is used to provide protons necessary to reduce oxygen. NAFION® 117 is a solid perflourinated copolymer available in the hydrogen form. NAFION® 117 is a perflourinated ion-exchange polymer having good thermal and chemical stability. The polymer electrolytes, like NAFION® 117, are permeable to cations, while rejecting anions.

The conductivity of the polymer electrolytes demonstrates a strong dependence on relative humidity due to hydrophilic nature of the electrolyte. Overall, the relative humidity plays an important part in sensor response because polymer electrolyte conductivity, and oxygen, carbon dioxide, and carbon monoxide permeability, are strongly related to the water content in the polymer electrolyte.

Temperature also is important because temperature effects the hydration of NAFION® 117 with the amount of water in the polymer electrolyte increasing as the temperature increases. See S. B. Lee, *J. Electrochem. Soc.*, Vol. 142, (1995) pages 157–160.

However, the relative humidity adds to the background response of the active sensor. Therefore, to successfully use a polymer electrolyte in a sensor to detect a predetermined gas in air, the conductivity dependence of the polymer electrolyte to relative humidity, and to temperature, had to be compensated. Previous investigators merely relied upon humidifying the tested air samples to a sufficiently high humidity such that the background response was essentially always the same.

In particular, the increase in conductivity of the polymer electrolyte with an increase in relative humidity results in an increase in sensor background and sensitivity (ppm/mV) with increasing relative humidity. In order to accurately determine the concentration of the predetermined gas in air, it is important to compensate for this relative humidity effect. In accordance with an important feature of the present invention, this compensation is accomplished by correcting the background signal, and the sensitivity of the signal, for relative humidity. The compensation can be done by means operatively connected to the active sensor and the reference sensor, such as a circuit or in software using a table giving the background and span as a function of the reference background current, wherein the response of the reference sensor correlated to, i.e., is subtracted from, the response of the active sensor.

In accordance with another important feature of the present invention, small signals previously have limited the usefulness of polymer electrolyte-containing sensors in gas detection. With small signals, i.e., low sensitivity, a change in response attributed to a change in relative humidity can correspond to a large change in apparent ppm levels of the predetermined gas. Therefore, compensation for the effect of relative humidity becomes more critical when the signal is small. For gases detected using low surface area electrodes, the small signal problem can be addressed by utilizing more complex electrode geometries, such as microelectrodes. Alternatively, and in accordance with an important feature of the present invention, high surface area electrodes have been developed to increase the signal. The high surface area electrodes provide an enhancement in sensitivity to a predetermined gas by a factor of up to about forty, and thereby overcome the small signal problem.

In particular, an electrochemical sensor of the present invention is illustrated in FIG. 1, wherein the sensor 10 comprises a substrate 12, a working electrode 14, and a counter electrode 16. FIG. 1 illustrates one configuration of either an active sensor or a reference sensor.

An amperometric electrochemical microsensor shown in FIG. 1 was prepared as follows. Working electrode 14 of dimensions 1.5 cm (centimeters)×0.14 cm, and counter electrode 16 of dimensions 1.5 cm×0.11 cm, were applied to substrate 12. The photolithographically defined electrodes 14 and 16 are made from high purity e-beam evaporated platinum 2000 Å thick deposited onto either an oxidized silicon or an alumina substrate 12 having a surface roughness of about 0.5 µm to 1 µm. Electrodes 14 and 16 have a thickness of about 250 to about 5000 Å, and preferably about 1000 to about 4000 Å. To achieve the full advantage of the present invention, the electrodes have a thickness of about 1500 to about 3000 Å. Electrodes prepared by depositing an evaporated electrode material on a substrate are examples of a "low surface area electrode." The deposition technique provides a very smooth, i.e., a flat, electrode surface.

Platinum electrodes 14 and 16 then were annealed at 650° C. for 1 hour in nitrogen to insure sufficient adhesion to substrate 12. A film of NAFION® 117 polymer electrolyte, in the hydrogen form and 1.3 micrometers thick, then was spin coated over electrodes 14 and 16 using a 5% solution in isopropanol. Next, the polymer electrolyte film was cured on electrodes 14 and 16 at 70° C. to improve the adhesion and toughness of the polymer electrolyte. Polymer electrolyte present on the bonding pads was removed using acetone, then isopropyl alcohol, followed by deionized water.

The polymer electrolyte film has a thickness of about 0.1 to about 5, and preferably 0.1 to about 4.5, micrometers. To achieve the full advantage of the present invention, the polymer electrolyte film is about 0.3 to about 4 micrometers thick. The specific thickness of the polymer electrolyte film is related to several variables, including the identity of the gas analyte, and the thickness can be determined by persons skilled in the art. Connecting wires (not shown) were attached using a silver-filled, conductive epoxy resin that cures below 75° C., which then was covered with a high vacuum insulating epoxy resin (Torr-Seal, TM Varian) that cured at room temperature in about 48 hours.

Sensors having the configuration illustrated in FIG. 1, and having electrodes made from platinum or gold on alumina substrates were prepared. Some of the platinum sensors were coated with NAFION® 117 polymer electrolyte and stored (i.e., low surface area sensors). The remaining platinum sensors were electroplated with a high surface area platinum (i.e., platinum black) using chloroplatinic acid and a current density of about 30 mA/cm$^2$ (milliamperes per square centimeter), then annealed, before coating the sensors with NAFION® 117 (i.e., high surface area sensors). Electrodes prepared by electroplating an electrode material on a substrate, or over an existing electrode, are examples of a "high surface area electrode." The electrolyte technique provides an electrode surface that is rougher than a low surface area electrode.

The sensors were tested by placing a sensor in a small sealed chamber having an atmosphere of a flowing gas system having carbon monoxide concentrations of 100 ppm to 1000 ppm in air. A total flow rate of one liter/minute was used for the exposure or vent. Relative humidity was controlled by passing a fraction of the diluent dry air through a bubbler, which then was mixed with the carbon monoxide stream and the remainder of the dry air. The relative humidity was measured using the relative humidity meter on the "Met-One" laser particle counter model 205-1-115-1. The data was logged on a personal computer using Keithley electrometers through an IEEE interface. The Keithly electrometers measured the direct output currents of the sensor or the output of a current to voltage converter circuit calibrated to 1 mV/nA (millivolt/nanoampere). All measurements were performed at room temperature (i.e., about 25° C.).

Figure 2:
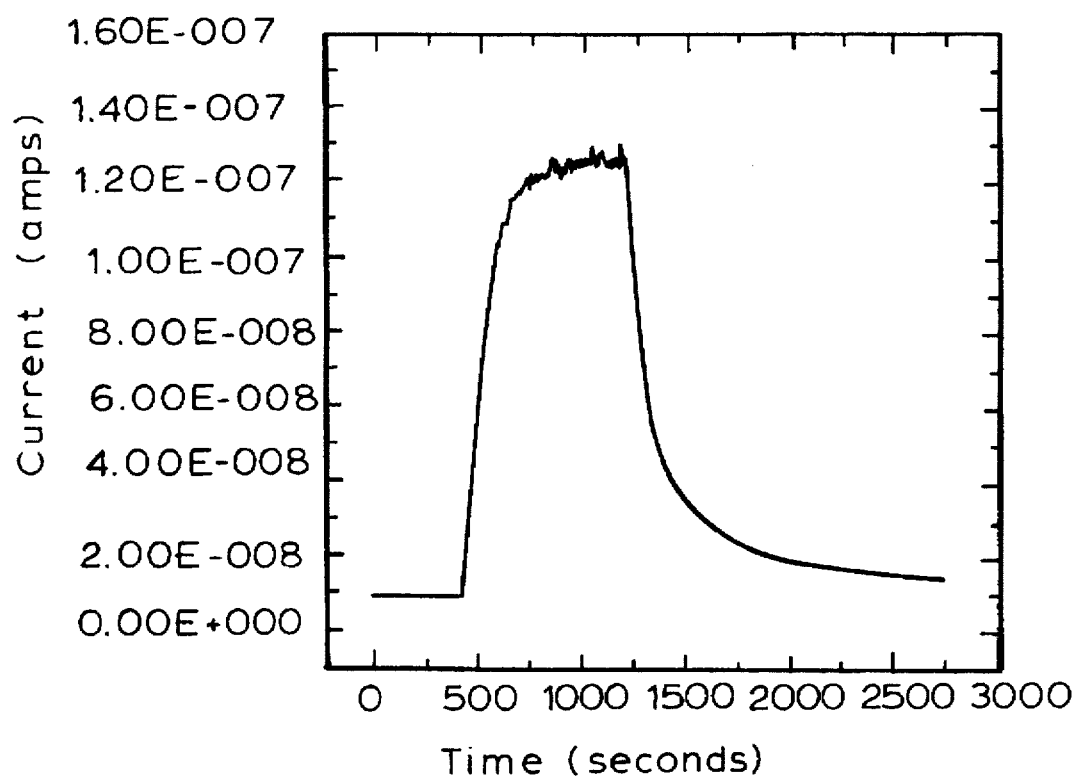
FIG. 2 is a plot of current (amps) vs. time (seconds) illustrating the real time response of a low surface area platinum sensor to 1100 ppm carbon monoxide at 66% relative humidity.
Figure 3:
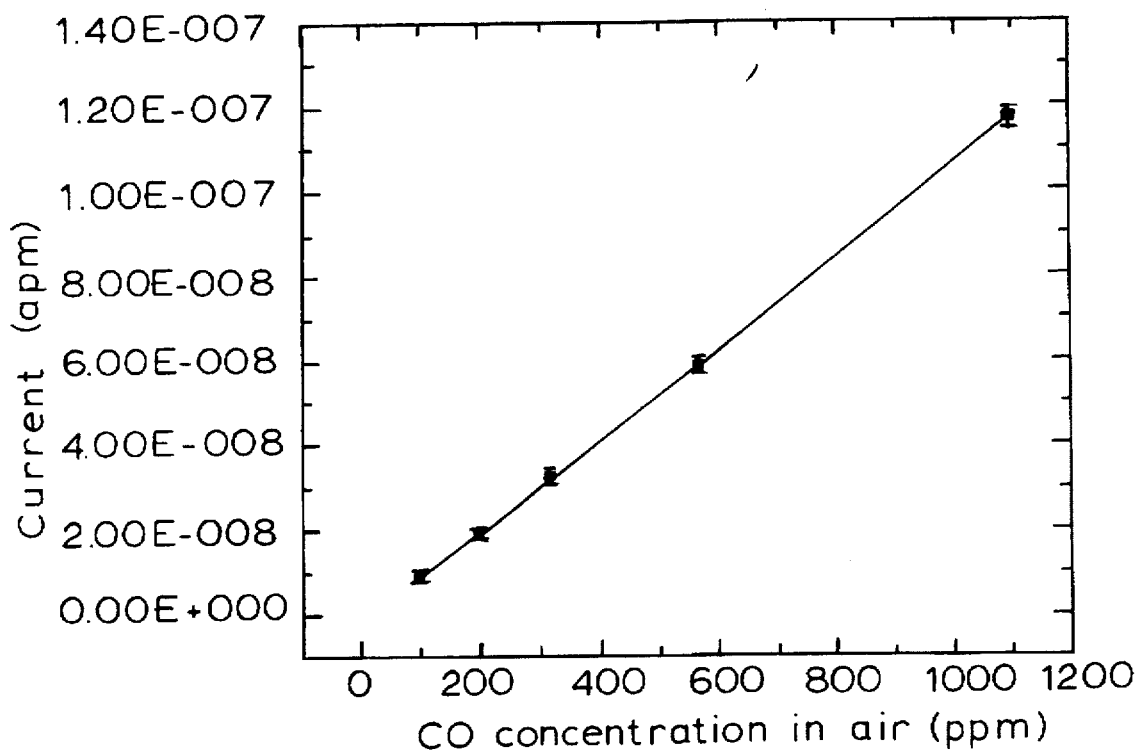
FIG. 3 is a plot of current (amps) vs. CO (carbon monoxide) concentration in air (ppm)
Figure 4:
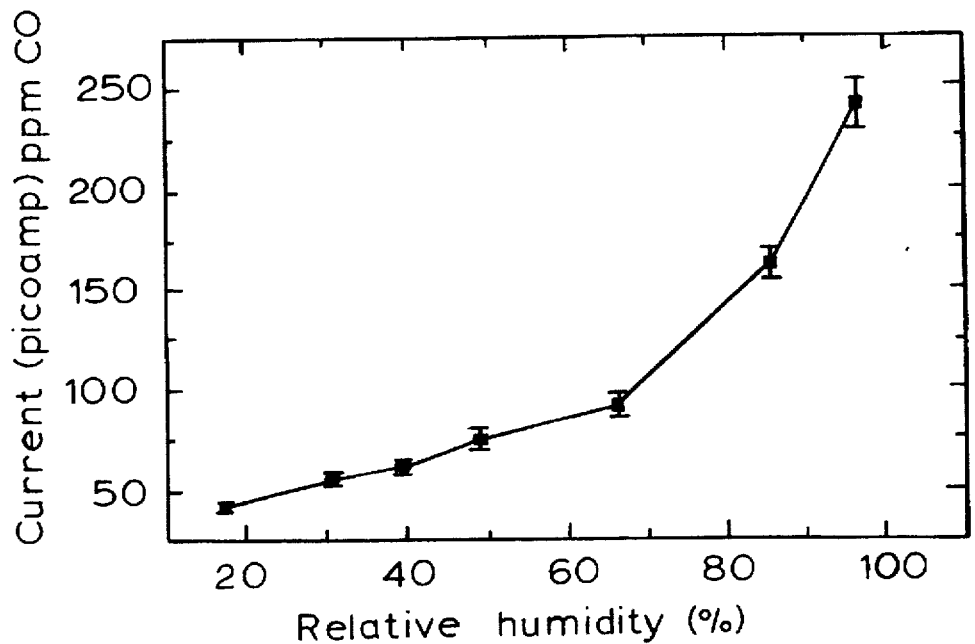
FIG. 4 is a plot of current (picoamp)/ppm CO vs. relative humidity at room temperature.

With respect to the low surface area sensors, the real time response (i.e., output current of the amperometric microsensor vs. time) of a low surface area platinum sensor to 1100 ppm carbon monoxide in air is shown in FIG. 2. The response time (from 10 to 90% of response) is about 2.5 minutes. The response is linear over the tested range (i.e., 100 to 1000 ppm carbon monoxide), as shown in FIG. 3, for a relative humidity of 66%. The slope of the line represents the sensitivity, in current/ppm, of the sensor at 66% relative humidity. The sensitivity of the sensor increases with relative humidity, as shown in FIG. 4.

Figure 5:
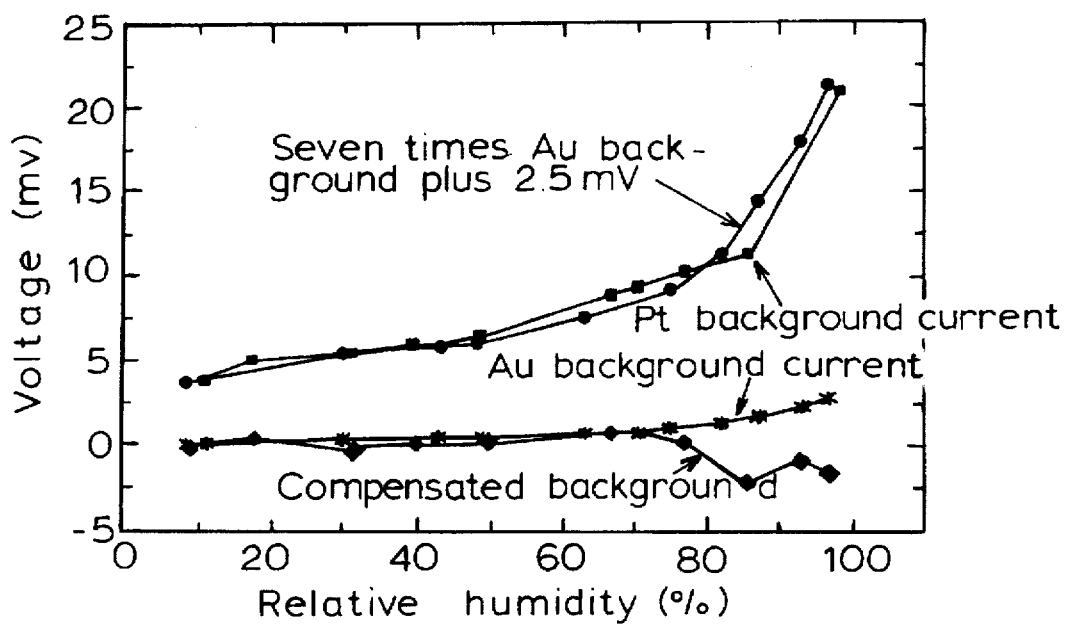
FIG. 5 is a plot of voltage (mV) vs. relative humidity (%) for a platinum-based active sensor and a gold-based reference sensor.

The background current for a platinum (Pt) gas sensor (upper curve) and a gold (Au) reference sensor, both having the configuration illustrated in FIG. 1, are shown in FIG. 5. FIG. 5 illustrates that the background current of the platinum-based sensor can be correlated to the response of the gold-based sensor. The background current of the platinum-based sensor is about equal to seven times the response of the gold-based sensor plus 2.5 nanoamps. The difference between this current and the platinum background is plotted as the compensated signal in FIG. 5. The compensation background plotted was calculated from 7 times the gold background current plus 2.5 mV, less the platinum background. The ideal is to a compensated baseline of 0 mV. The deviation from zero above 85% relative humidity is attributed to condensation effects in the apparatus.

Figure 6:
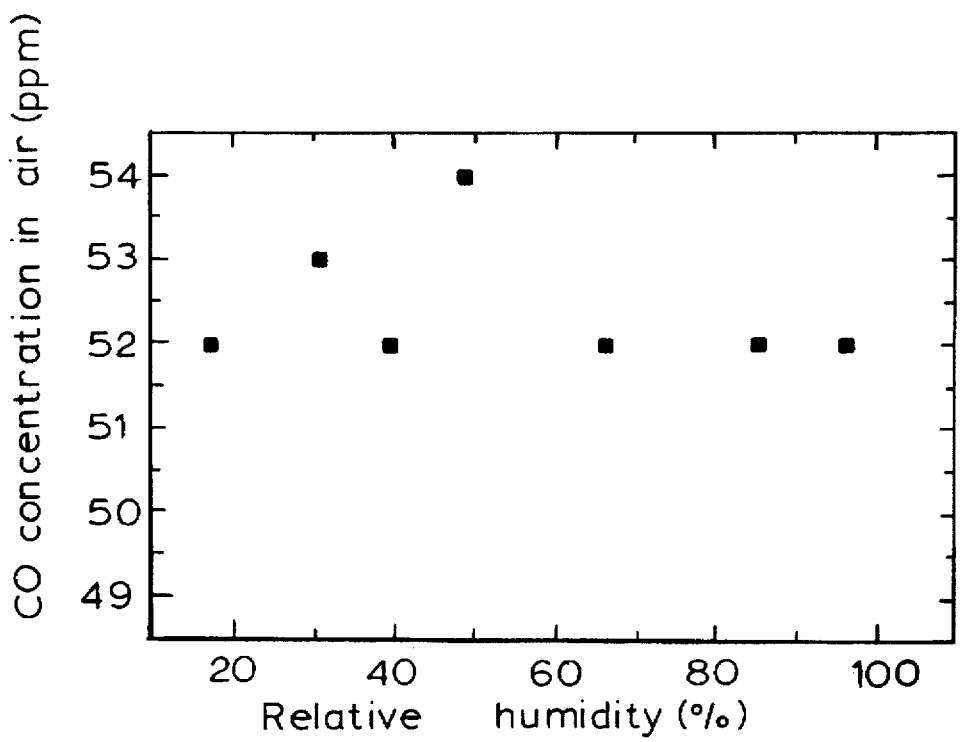
FIG. 6 is a plot of carbon monoxide (CO) concentration in air (ppm) vs. relative humidity (%), wherein the raw data was compensated for relative humidity effects.

An experiment was conducted in which low surface area platinum and gold sensors were exposed to 50 ppm carbon monoxide over a broad relative humidity range. Using the sensitivity and background data in FIGS. 4 and 5, the effects of relative humidity were compensated, and carbon monoxide concentration was determined and plotted in FIG. 6. In this experiment, the concentration of carbon dioxide was determined to within about 4 ppm.

Figure 7:
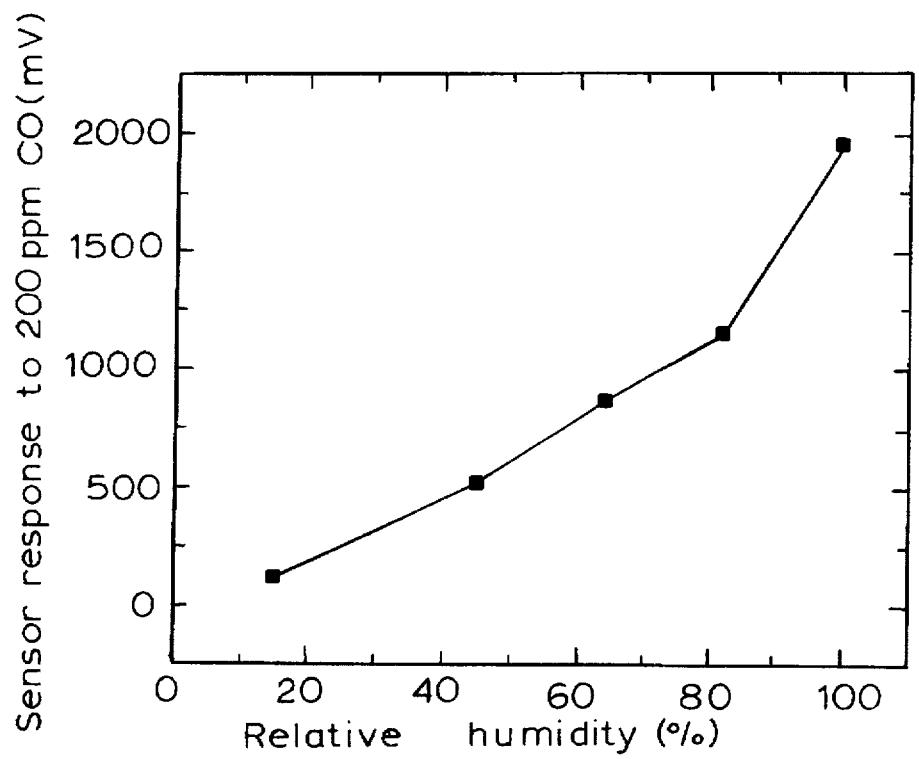
FIG. 7 is a plot of the total sensor response (mV) to 200 ppm carbon monoxide vs. relative humidity for a high surface area platinum sensor.
Figure 8:
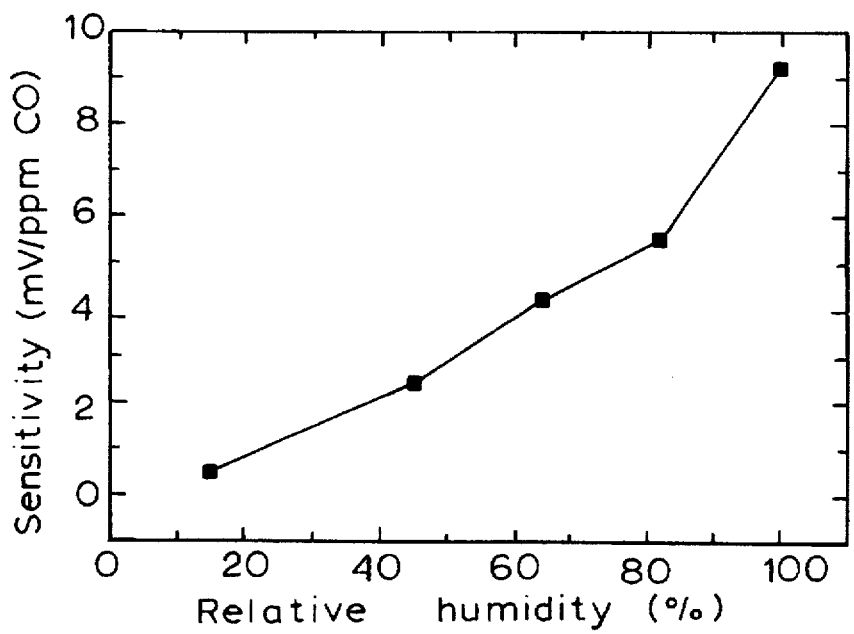
FIG. 8 is a plot of sensitivity (mV/ppm carbon monoxide) vs. relative humidity (%) for a high surface area sensor.
Figure 9:
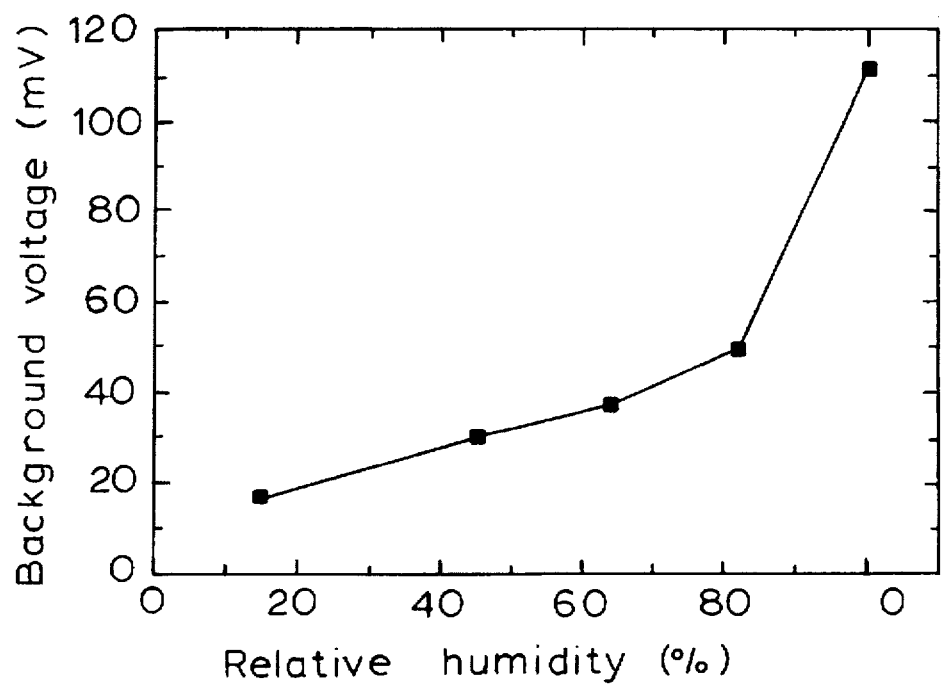
FIG. 9 is a plot of background voltage (mV) vs. relative humidity (%) for a high surface area sensor.
Figure 10:
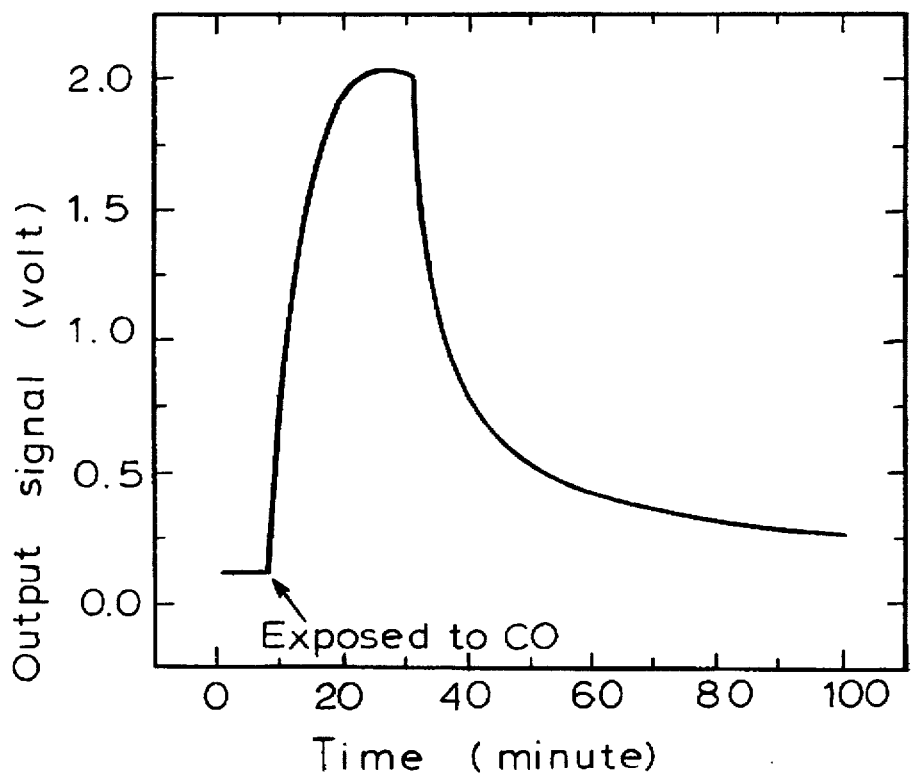
FIG. 10 is a plot of output signal (volt) vs. time (minutes) for a high surface area platinum sensor to 200 ppm carbon monoxide in air.

With respect to the high surface area platinum black sensors, these sensors were exposed to 200 ppm carbon monoxide. The measured total current is shown in FIG. 7. The signal increased by a factor of 20 over the range of relative humidities studied, i.e., 15% to 100%. In order to compensate for relative humidity, the sensitivity and background as functions of relative humidity, as shown in FIGS. 8 and 9, respectively, were determined. At high relative humidity, the sensitivity of the high surface area sensor to carbon monoxide is about 40 times greater than the sensitivity of the low surface area sensor. On the other hand, the background current of the high surface area sensor is only four times greater than the low surface area sensor. The real time response of the high surface area sensor to 200 ppm carbon monoxide in air at 100% relative humidity is shown in FIG. 10.

The above experiment and the FIGS. show that electrochemical sensors comprising either low surface area or high surface area platinum electrodes and low surface gold electrodes, each coated with a polymer electrolyte, have been prepared and used to detect and quantify a predetermined gas, e.g., carbon monoxide. It further has been shown that high surface area electrodes are about 40 times more sensitive to the predetermined gas than low surface area electrodes.

Furthermore, the effects of relative humidity can be eliminated by simultaneously measuring data from the active and reference sensors, and correlating and correcting the data to account for a background response attributed to relative humidity. The sensors of the present invention also exhibit a stable response over time and temperature, and over a changing relative humidity.

In summary, an electrochemical detector for a predetermined gas in air comprises an active sensor and a reference sensor. The active sensor comprises: (1) high surface area or low surface area electrodes that are sensitive to the predetermined gas of interest, e.g., for the detection of carbon monoxide, platinum can be used as the electrode material of the active sensor, and (2) a coating of a polymer electrolyte over the electrodes. The reference sensor comprises: (1) electrodes that are insensitive to the predetermined gas of interest, e.g., for carbon monoxide, gold can be used as the electrode material of the reference sensors, and (2) a coating of the polymer electrode over the electrodes.

Several different designs are envisioned for the reference sensors. The optimum design ultimately depends on the identity of the predetermined gas to be detected and the variability of the background current with respect to relative humidity. For illustrative purposes only, the following discussion illustrates embodiments of reference sensors used in the detection of carbon monoxide.

In one embodiment, the response of the active sensor is compensated by a reference sensor having an identical design as the active sensor, except the platinum electrodes of the active sensor are replaced by gold electrodes. The gold electrodes of the reference sensor are not sensitive to carbon monoxide, but are sensitive to ambient moisture, i.e., relative humidity. Hence, the background current measured by the active sensor is approximately the same as the background current measured by the reference sensor. The background current of the reference sensor, therefore, is used as a measure of the effect of relative humidity, and is subtracted from the current exhibited by the active sensor to compensate for the effect of relative humidity. This embodiment also compensates for change in background current with changing temperature, therefore, compensating for the effects of temperature.

In another embodiment, the reference sensor for the detection of carbon dioxide comprises platinum electrodes having a thicker coating of polymer electrolyte than the platinum electrodes of the active sensor. The thick layer of polymer electrolyte in the reference sensor prevents detection of carbon monoxide by the platinum, and, therefore, the reference sensor measures only the effects of relative humidity and temperature.

In yet another embodiment, the reference sensor comprises platinum electrodes having a very small response to carbon monoxide. This is achieved by making the working and counter platinum electrodes of the reference sensor small and symmetrical in design. Carbon monoxide sensitivity is related to the surface area of the working electrode, and, therefore, a sensor having a working electrode with large surface area shows a greater sensitivity to carbon monoxide. Hence, the reference sensor measures only the effects of relative humidity and temperature, which can be subtracted from the response of the active sensor.

In another embodiment, the reference sensor comprises platinum electrodes conditioned to exhibit a negative response to carbon monoxide (i.e., the current decreases when carbon monoxide is present). A negative response to carbon dioxide can be achieved, for example, by biasing the platinum electrodes at a specific potential. This technique eliminates the relative humidity effects, and also increases the size of the signal. Because one sensor (i.e., the active carbon monoxide sensor) shows a positive response and the second sensor (the reference sensor) shows a negative response to the presence of carbon monoxide, the difference between two responses is increased.

In addition, there also is a change in the sensitivity of the sensor with changing relative humidity. This effect can be compensated by using the value of the current from the reference sensor which correlates to the relative humidity. An additional temperature measurement, which can be done by a diode or other temperature-sensing means, also can be used for full compensation of temperature effects. The gas detector operates by making a differential measurement. The current from the reference sensor is subtracted from the current of the active sensor. The net current is proportional to, and correlated to, the concentration of a predetermined gas in air.

Other investigators have made microfabricated electrochemical sensors. However, each design had problems and disadvantages that prevented commercialization. The present electrochemical sensors have overcome these problems. For example, prior sensors using a polymer electrolytes required the addition of moisture to operate because the polymer electrolytes are proton-conducting polymers. In the absence of uniform humidification, measurement errors resulted. In many cases, this problem was addressed by a 100% humidification of the gas sample before exposure to the sensor. This is a common approach when using polymer electrolytes, but is not practical in many cases. Humidification has the advantage of eliminating ambient relative humidity effects on the signal, but is an additional process step and has a disadvantage in that the water supply must be replenished periodically.

The signal from prior sensors was not compensated for temperature or relative humidity effects. Therefore, if the sample gas was not humidified, the sensor responded to relative humidity and the signal was effected. Without compensation for relative humidity and temperature, the sensor did not provide accurate gas detection results. No present gas detector has an ability to compensate for relative humidity or temperature.

Prior sensors using a polymer electrolyte suffered from an inability to provide repeatable results in the detection of a predetermined gas. In accordance with an important feature of the present invention, the repeatability problem has been overcome by exposing the electrodes coated with the polymer electrolyte to highly humidified air (e.g., about 95%) for 24 hours or more. During this time, sufficient moisture permeates the polymer electrolyte to essentially saturate the polymer electrolyte. Sufficient moisture, therefore, is available to conduct protons and transport oxygen, carbon monoxide, and carbon dioxide through the polymer electrolyte, and, accordingly, provide repeatable results.

Another problem encountered in prior sensors was insufficient adherence of the electrodes to the substrate. This problem has been overcome by subjecting the electrodes to a thermal processing step. Previous investigators used adhesion-promoting layers to provide electrodes that adhered to a substrate surface, particularly during long-term exposure to the humidified acidic electrolyte. The common adhesion-promoting layers were layers of chromium and titanium. However, these materials are electrochemically active and can corrode during operation of the sensor, thereby limiting sensor lifetime to about 1 month.

The present invention eliminates the adhesion-promoting layers by using a thermal processing step. In this step, a wafer comprising platinum electrodes on a silicon dioxide substrate is subjected to a high temperature anneal at approximately 650° C., in an inert atmosphere. It has been theorized that this step causes the formation of platinum silicide, which is known to form when platinum is annealed at temperatures about 450° C. Platinum silicide is known as a very stable interface material. This annealing step also has been used to adhere platinum electrodes on alumina substrates.

In addition, previous researchers using a spin coated polymer electrolyte reported problems with the stability of such films. In addition, a gradual decrease in the sensor sensitivity due to a conductivity decrease of the polymer electrolyte has been reported. An attempt to correct the problem by the addition of a stabilizer that coated the surface of the polymer electrolyte was unsuccessful and further reduced the sensitivity of the sensor.

The present electrochemical sensor does not exhibit a stability problem because the polymer electrolyte is cured after deposition of the polymer electrolyte on the electrodes by heating the coated electrodes in air. The cure is performed at about 50° C. to about 150° C. for about 5 minutes to about 120 minutes. Preferably, the polymer electrolyte is cured at about 60° C. to about 90° C. for about 40 minutes to about 100 minutes.

The curing step provides two beneficial effects. First, curing stabilizes the polymer electrolyte film by causing the polymer electrolyte film surface to become tougher and more durable. Second, curing improves adhesion of the polymer electrolyte to the substrate. This is an important feature because an increase in the relative humidity causes the polymer electrolyte to expand. As the relative humidity levels fluctuate, the polymer electrolyte expands and contracts, with an overall change in dimensions of about 12%. Repeated relative humidity cycling can cause the polymer electrolyte film to detach from the surface of the substrate in regions and to form overlapping regions. After curing, no overlapping regions were observed, nor was detachment of the polymer electrolyte film from the substrate observed after several relative humidity cycles or after placing drops of water on the polymer electrolyte film.

Previous researchers also reported weak response signals for the predetermined gas concentration range of interest. The present electrochemical sensor overcomes the problem of weak response signals by applying a suitable thickness of polymer electrolyte on the electrodes in relation to the thickness of the electrodes, and by having a suitable spacing between the working and counter electrodes.

Although previous researchers employed polymer electrolyte films in electrochemical sensors, the effects of the polymer electrolyte film thickness on the operation of the sensor were not recognized. An experiment directed to the effects of polymer electrolyte film thickness showed that there is an optimum polymer electrolyte film thickness which is related to:

(a) sensor geometry. For example, spacing between the working electrode and the counter electrode is important because the total resistance between the working electrode and the counter electrode depends on the geometry, as well as the thickness of the polymer electrolyte film.

(b) predetermined gas to be detected. This dependence occurs for several reasons. For example, the gas of interest must diffuse through the polymer electrolyte film to reach the electrode-electrolyte interface (i.e., the triple point interface) in order to generate an electrochemical signal. The thicker the polymer electrolyte film, the more difficult for the gas and moisture diffusion to occur.

(c) bias. If the sensor is to be operated in a selective manner, then the bias is determined primarily by the identity of the gas to be detected. Measurements have shown that, for a given gas and bias voltage, no signal is observed for some polymer electrolyte thicknesses.

Polymer electrolyte films that are too thick, therefore, result in a sensor having little or no sensitivity. The reduced sensitivity primarily is due to the inability of moisture and gases to penetrate into the polymer electrolyte films and contact the electrodes. Because moisture is required for ionic conduction in the polymer electrolyte, the polymer electrolyte nearest the electrodes has a higher resistivity than the polymer electrolyte film near the exterior surface of the. If the polymer electrolyte film is too thick, the predetermined gas also has a reduced concentration near the electrode, thereby resulting in a reduced sensor signal. As stated above, the diffusion coefficient of the predetermined gas determines the amount of predetermined gas that reaches the electrode-electrolyte interface.

If the polymer electrolyte film is too thin, the resistance of the film is high and there is insufficient ionic conductivity to support to a sufficiently large sensor signal current. Hence, a thin film results in a sensor having reduced or no sensitivity to the predetermined gas.

The previous problem of low signal levels has been overcome by using a high surface area electrodes. The photolithographically defined platinum electrodes are prepared by patterning an e-beam evaporated electrode material, such as platinum, on a substrate. These are low surface area electrodes. Onto a low surface area electrode, a high surface area electrode material, such as platinum, commonly called platinum black, was electrodeposited. This process conventionally was done by electroplating in chloroplatinic acid. The resulting high surface area electrodes have shown increase in signal, i.e., in sensitivity, by about a factor of 40 over low surface area electrodes. In addition, the background currents of the high surface area sensors do not increase significantly over the background amounts of the low surface area electrodes. Accordingly, compensation for relative humidity is facilitated using a high surface area electrode. Thus, high surface area platinum electrodes have significant advantages for use in a carbon monoxide sensor.

The thickness of the electrodeposited platinum black film is about 0.1 to about 3, and preferably 0.2 to about 2, microns. To achieve the full advantage of the present invention, the thickness of the platinum black film is about 0.5 to about 1.5 microns. In order to improve the adhesion of the platinum black to the platinum, the platinum black film is annealed at about 650° C. for about 1 hour in dry nitrogen.

Although the above discussion is directed primarily to the detection and measurement of carbon monoxide in air, the electrochemical sensors of the present invention can be readily adapted for the detection and measurement of other predetermined gases in air. The design of an electrochemical sensor for a particular predetermined gas is related to several variables, for example:

(1) the electrode material, such as a noble metal, like platinum, or gold, or other electrode material, like carbon.

(2) the surface area of the electrode. Specifically, the electrode can have a high surface area or a low surface area. Direct evaporation or sputtering of the electrode materials onto the substrate yields low surface metal electrodes. Electrodeposition can provide a high surface area electrode. For some gases, such as carbon monoxide, a high surface area electrode gives higher catalytic activity and, therefore, greater sensitivity. High surface area platinum, gold, and carbon electrodes have been prepared.

(3) the thickness of the polymer electrolyte film. The specific polymer electrolyte film thickness depends in part on the diffusivity of the predetermined gas through the polymer electrolyte. Persons skilled in the art of designed electrochemical sensors are able to determine an appropriate polymer electrolyte film thickness in relation to the diffusion coefficient of the predetermined gas and the properties of the polymer electrolyte.

(4) the bias applied to the electrodes. The bias applied to the electrodes is related to the particular chemical reactions occurring at the electrodes. The chemical reactions involve the predetermined gas, and is known to persons skilled in the art. Likewise, the bias applied to the electrodes is known, or can be determined by persons skilled in the art. With respect to carbon monoxide, for example, the optimum bias voltage is −0.3 to +0.3 volts.

(5) the geometry of the electrodes. Electrode geometry can be, for example, (a) a simple block electrode, such as a rectangle, or (b) a shape designed to have a high perimeter because certain gases show enhanced response with high perimeter electrodes. This phenomena is explained by the observation that some reactions at the electrode apparently occur at the triple point perimeter of the electrode where the electrode material, predetermined gas, and polymer electrolyte meet. One method of accomplishing a high perimeter is introducing several "windows" into a solid electrode. Another method is to use of conductive ultrathin metal films, such as porous films of interconnected islands.

Amperometric electrochemical gas sensors, therefore, can be designed to detect several different gases. For example, high surface area platinum-based sensors can be used for carbon monoxide sensing. A low surface area gold or platinum electrode can be effectively used in hydrogen sulfide or nitrogen dioxide sensors because reactivity of the electrodes is high for hydrogen sulfide and nitrogen dioxide, but is low for carbon monoxide. A selective detection and measurement of a predetermined gas, therefore, is possible. High surface area platinum electrodes have broad catalytic activity and can, therefore, be used to detect many different gases in air, including carbon monoxide, hydrogen sulfide, nitric oxide, nitrogen dioxide, sulfur dioxides, hydrocarbons (e.g., acetylene), formaldehyde, and ethanol. High surface area gold electrodes can be used to detect hydrogen sulfide, sulfur dioxide, and nitrogen oxides ($NO_x$). Low surface area gold electrodes can be used to detect low gas concentrations where low background signals are required.

A small surface area electrode is planar and has a surface area essentially equal to the area of the substrate covered by the electrode. A high surface area electrode has a surface area at least three times greater than the area of the substrate covered by the electrode.

We claim:

1. An electrochemical sensor to detect the presence and concentration of carbon monoxide in air, said sensor comprising:

(a) a substrate;

(b) a working electrode deposited on a surface of the substrate;

(c) a counter electrode deposited on a surface of the substrate; and (d) a film of a polymer electrolyte applied over the working and counter electrodes, wherein the sensor is free of a reference electrode and wherein the working electrode comprises a first layer of gold, platinum, or carbon in contact with the substrate, said first layer having a thickness of about 250 to about 5000 Å, and a second high surface area layer of platinum in contact with the first layer.

2. The sensor of claim 1 wherein the substrate comprises silicon dioxide, alumina, or a polymer.

3. The sensor of claim 1 wherein the second high surface area layer is electrodeposited on the first layer.

4. The sensor of claim 1 wherein the film of polymer electrolyte is about 0.1 to about 5 micrometers thick.

5. The sensor of claim 1 having a sensitivity to carbon monoxide up to about 40 times greater than a sensor containing two low surface area working and counter electrodes.

6. The sensor of claim 1 wherein the counter electrode is a high surface area electrode.

* * * * *